United States Patent
Wysong et al.

[19]

[11] Patent Number: 6,015,773
[45] Date of Patent: Jan. 18, 2000

[54] CROP PROTECTION COMPOSITION COMPRISING A CROP PROTECTION SOLID PARTICLE COATED WITH WATER-INSOLUBLE COATING MATERIAL AND A CROP PROTECTION MIXTURE COMPRISING THE SAME

[75] Inventors: Robert David Wysong; George Bernard Beestman, both of Wilmington; George Alan Schurr, Newark, all of Del.

[73] Assignee: E. I. du Pont de Nemours and Company, Wilmington, Del.

[21] Appl. No.: 09/029,200

[22] PCT Filed: Aug. 23, 1996

[86] PCT No.: PCT/US96/13677

§ 371 Date: Feb. 25, 1998

§ 102(e) Date: Feb. 25, 1998

[87] PCT Pub. No.: WO97/07676

PCT Pub. Date: Mar. 6, 1997

Related U.S. Application Data

[60] Provisional application No. 60/002,901, Aug. 29, 1995.

[51] Int. Cl.$^7$ ..................................................... A01N 25/28
[52] U.S. Cl. .......................... 504/116; 424/408; 424/490; 424/496; 424/498; 514/963
[58] Field of Search ............................ 504/116; 424/408, 424/490, 496, 498; 514/963

[56] References Cited

U.S. PATENT DOCUMENTS 5,589,194  12/1996  Tsuei et al. .............................. 424/497
5,652,196  7/1997  Luthra et al. ............................ 504/116

FOREIGN PATENT DOCUMENTS

| 0 379 379 A2 | 7/1990 | European Pat. Off. . |
| 0 548 901 A1 | 6/1993 | European Pat. Off. . |
| 0 344 248 B1 | 3/1995 | European Pat. Off. ....... A01N 25/26 |
| 2 684 265 | 6/1993 | France . |
| 29 40 263 A1 | 5/1981 | Germany . |
| WO A 94 22302 | 10/1994 | WIPO . |

OTHER PUBLICATIONS

Sliwka, Wolfgan. "Microencapsulation" Angew. Chem. Internat. Edit. 14(8):539–550, 1975.

*Primary Examiner*—S. Mark Clardy

[57] ABSTRACT

A composition comprising a mononucleate solid crop protection particle coated with a water-insoluble coating material has a diameter in the range of 0.5 to 50μ. This composition is made by a process which results in substantial non-agglomeration of the coated particles. In a particular embodiment, a crop protection composition comprises a mononucleate solid crop protection particle coated with either wood rosin, rosin derivatives, waxes, fatty derivatives, sterols, long-chain sterol esters and sulfur. Alternatively, the coating material may be a water-insoluble synthetic latex polymer. The composition may be used in a mixture which also includes a crop protection chemical partner comprising a solid particle. The partner ordinarily degrades the solid crop protection particle when stored or aged together as a solid particle mixture. However, when the composition solid particle is coated, this degradation is prevented.

20 Claims, 2 Drawing Sheets

CROP PROTECTION COMPOSITION COMPRISING A CROP PROTECTION SOLID PARTICLE COATED WITH WATER-INSOLUBLE COATING MATERIAL AND A CROP PROTECTION MIXTURE COMPRISING THE SAME

This application is a filing under 35 U.S.C. 371 of PCT/US96/13677 filed Aug. 23, 1996 which claims the priority benefit of U.S. Provisional Application 60/002,901, filed Aug. 29, 1995.

BACKGROUND OF THE INVENTION

1. Field of the Invention

This invention relates to a crop protection composition comprising a crop protection solid particle coated with a water-insoluble coating material. More specifically, this invention relates to a crop protection composition comprising an individual, mononucleate solid particle, which may be either a chemical crop protection solid particle, such as a herbicide, an acaricide, an insecticide, a miticide, a plant growth regulator, a fungicide or a nematicide, or a microbial crop protection solid particle, such as beneficial viruses, nematodes, fungi, bacteria or protozoa, coated with a water-insoluble coating material. The chemical or the microbial crop protection particle may be coated with either wood rosin, rosin derivatives, waxes, fatty derivatives, sterols, long-chain sterol esters or sulfur. Alternatively, the chemical or microbial crop protection particle may be coated with a water-insoluble latex polymer. In addition, the present invention relates to a mixture of such crop protection compositions with a partner which is also a solid particle.

2. Description of the Related Art

Encapsulation of an active component, such as a biocide, is disclosed in International Publication Number WO 95/08322. In this publication, "microcapsules" are prepared by dispersing or dissolving an active component or components in a solid matrix-forming material that has been thermally softened to form an encapsulation composition. The encapsulation composition is injected as an intact stream into a quenching liquid to provide solid microcapsules. What is termed "microcapsules" prepared by this method are really a plurality of particles randomly dispersed through a solidified droplet of coating material. These microcapsules do not have a single, mononucleate solid particle as a core surrounded by a wall of coating material. Moreover, the diameter of such microcapsules is not disclosed.

Large crop protection solid particles coated with water insoluble materials (i.e., particles having a diameter say, greater than 50 micrometers) clog screens and nozzles and thus, are not sprayable onto crops in the field. Known methods of coating or encapsulating small particles, (say, less than 50 micrometers) have serious process limitations. For instance, spray drying results in aggregates of tiny particles, or agglomerates, and requires solvent handling. Moreover, such agglomeration reduces the biological efficacy of the coated particles, since not all the particles are available for activity. Fluid bed coating is unsuited to small particles, such as powders, because tiny particles are difficult to fluidize in a fluid bed because interparticle forces are greater than those resulting from the action of the gas in the fluid bed. Particles are classified as Geldart Groups A, B, C and D. Geldart Group C powders, i.e., those less than 20 micrometers in diameter, are very difficult to fluidize. See Fluidization Engineering, Second Edition, Daizo Kunil and Octave Levenspiel, Butterworth-Heinmann Series in Chemical Engineering, ISBN 0-409-90233-0, pp 77–79. The Wurster process is not suited to coating small particles. Spinning disc processes are limited to particles larger than 50 micrometers, and require coating recovery/recycle steps. Such processes are also unsuited to non-spherical particle shapes and require a tight particle size range for uniform coating. With concentric nozzles, active ingredients are propelled through a coating composition. However, such a technique is unsuited to coating individual particles, and aggregates result. Moreover, coating recovery systems are required with concentric nozzles. Finally, chemical coacervation is a batch-type process that produces fine particle aggregates, is a dilute process, and requires extensive solvent recovery.

Coated particles made from the above-described techniques are also known. For instance, published European Patent Application 0 548 901 A1 discloses a microcapsule comprising agricultural active ingredients which is made by spray drying, which produces agglomerates as noted above. Moreover, this publication discloses the use of water soluble coatings, which can be hygroscopic and which are not useful for controlled release. European Patent Application 0 379 379 A2 discloses coated agrochemical and other particulate compositions, where the coating is formed by coacervation from at least two water soluble coacervating polymers. As noted above, coacervation requires extensive solvent recovery. Moreover, the '379 publication is directed toward coating liquid actives, which coated liquid actives have less tendency to settle in water than solids. Published International Application WO 94/22302 discloses coated biologically active particles and a process for making such particles by forming an aqueous suspension, emulsion or solution of a polymer or a polymer-forming precursor which is used for coating the suspended active particle. This coating process is not able to entirely coat a particle in one pass, as evidenced by the fact that a second coating layer is necessary in order to coat the areas which are not coated by the first coating layer. Published International Application WO 89/03638 discloses a pesticide composite composed of a substrate and a film of sulfonated polymer coating. The substrate is relatively large in size, i.e., 1–10 mm. (1,000 to 10,000 micrometers). At least one surface of the substrate is coated with a film of sulfonated polymer dissolved in a solvent system.

All of the publications discussed in the paragraph above require the material to be coated to first be suspended in a liquid to achieve coating, thus creating difficult solids recovery problems and generating large process waste streams. In addition, if such processes require water as the liquid, they cannot encapsulate water soluble particles.

Thus, there exists a need for coated crop protection solid particles having a very small diameter, say less than 50 micrometers, and which are non-agglomerated so that they may be sprayed without clogging a nozzle or screen. In addition, there exists a need for developing a process for coating or encapsulating particles with very small diameters, say less than 50 micrometers, which results in a high yield of small coated, yet non-agglomerated particles. In addition, there exists a need for a process which does not have attendant solids recovery problems or large process waste streams. Moreover, there exists a need for developing a process which can encapsulate water soluble solid particles, and for the resulting coated solid particles.

SUMMARY OF THE INVENTION

The present invention solves the problems of the prior art by providing a non-agglomerated crop protection composition where the diameter of the composition is very small, i.e., in the range of 0.5 to 50 micrometers. The coated solid particles of the present invention have an increased biological efficacy as compared to agglomerated particles, since all the non-agglomerated particles are available for activity. Moreover, the coated solid particles of the present invention are made by a process which results in a higher percentage of small coated particles than do processes of the prior art.

This non-agglomeration is a result of the process by which the composition is made, which allows a solid particle to be directly coated with a coating material which is in the form of a melt, without having to be suspended in a liquid. Thus, this process allows for encapsulation of water-soluble solid particles. However, the coating material of the present invention need not be limited to a melt, but may also be in the form of a solution or a slurry, which may be aqueous, where the coating material is either dissolved or undissolved in a liquid, such as water, respectively.

The small-diameter, non-agglomerated coated solid particles of the crop protection composition of the present invention may be sprayed in a sprayer, without clogging the nozzle of the sprayer. In addition, with the present invention unstable, as well as stable, compounds are able to be isolated in a solid formulation. The crop protection composition of the present invention has a low acute toxicity during transfer, or even during spray application. Such a crop protection composition regulates soil mobility of active compounds in soils. With the crop protection composition of the present invention, application rates are reduced, and the selectivity between crops and weeds is improved. In addition, the crop protection composition of the present invention provides protection of microbials, both on the shelf and in the field environment.

Moreover, the present invention allows a crop protection composition to be mixed with a partner which ordinarily chemically degrades the crop protection composition when stored or aged together as a mixture. Thus, with the crop protection composition of the present invention, chemically unstable compounds are protected from hydrolysis, photolysis or other forms of degradation. Accordingly, the stable mixture of the present invention provides a broader spectrum of weed control, resistance to degradation, and possibilities for synergism.

To achieve the foregoing solutions and advantages, there is provided a crop protection composition comprising a mononucleate crop protection solid particle coated with a water-insoluble coating material, wherein the coating material is selected from the group consisting of: wood rosin, rosin derivatives, waxes, fatty derivatives, sterols, long-chain sterol esters and sulfur, and the diameter of the crop protection composition is in the range of 0.5 to 50 micrometers.

Also in accordance with the present invention, there is provided a crop protection composition comprising a mononucleate crop protection solid particle coated with a water-insoluble coating material, wherein the coating material is a synthetic latex polymer selected from the group consisting of: a homopolymer of a first group of monomers and a co-polymer made from the first group of monomers combined with at least one monomer from a second group of monomers, and the diameter of the crop protection composition is in the range of 0.5 to 50 micrometers.

Also in accordance with the present invention, there is provided a crop protection composition, comprising a mononucleate crop protection solid particle coated with a water-insoluble coating material, wherein the coating material is a synthetic latex polymer selected from the group consisting of: poly(ethylene terephthalate), polyamide resin, synthetic polyterpene, synthetic poly(beta-pinene) and cellulose esters, and the diameter of the crop protection composition is in the range of 0.5 to 50 micrometers.

Further in accordance with the present invention, there is provided a crop protection mixture, including a crop protection composition comprising a crop protection partner comprising a solid particle; and a crop protection composition as described in any of the three paragraphs above.

DETAILED DESCRIPTION OF THE PREFERRED EMBODIMENTS

Figure 1:
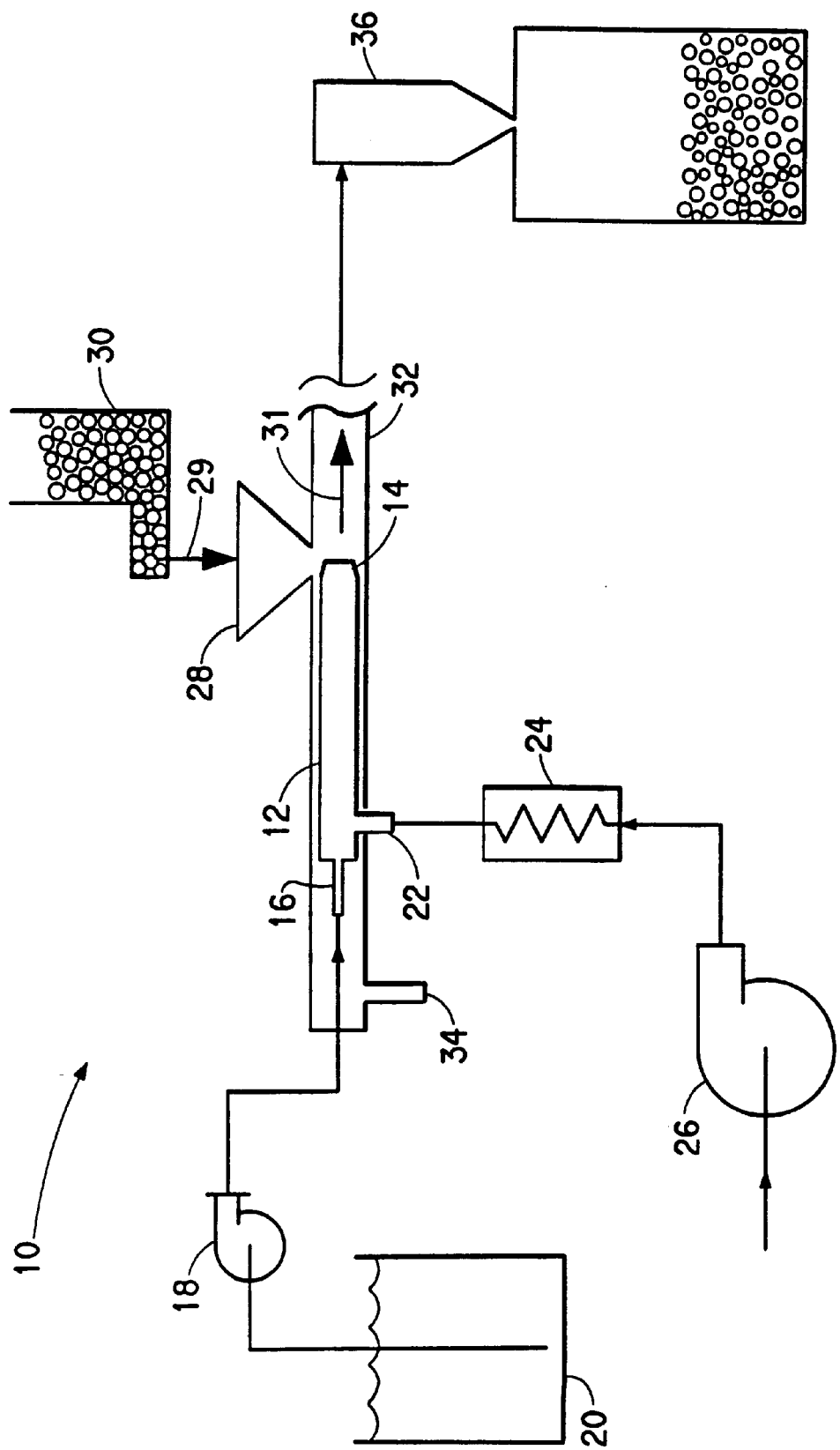
FIG. 1 is a schematic diagram of a portion of the apparatus in accordance with the present invention.

In accordance with a first embodiment of the present invention, there is provided a crop protection composition comprising a mononucleate solid crop protection particle coated with a water-insoluble coating material. In one version of the first embodiment, the water-insoluble coating material may comprise either wood rosin, rosin derivatives, waxes, fatty derivatives, sterols, long-chain sterol esters or sulfur. In addition, the coating material may also be a mixture of any of these materials, except for sulfur, and it may comprise other components. The diameter of the composition, that is, the final coated particle, is in the range of 0.5 to 50 micrometers (m), and preferably less than 30 micrometers. The coating is thin enough to make a negligible difference in the diameter of the solid particle after it is coated, as compared to before it is coated. For example, assuming the same density for the coating material and the solid particle, for a coating which is 5% by weight of the composition, the thickness of the coating material is 0.87% of the diameter of the solid particle, uncoated. For a coating which is 10% by weight of the composition, the thickness of the coating material is 1.7% of the diameter of the solid particle, uncoated. For a coating which is 50% by weight of the composition, the thickness of the coating material is 11.8% of the diameter of the solid particle, uncoated.

With respect to the particular coating materials, the rosin derivatives may be any of the following: partially dimerized rosin, partially hydrogenated rosin, salts of divalent metals, salts of tri-valent metals, adducts of maleic acid/anhydride, adducts of fumaric acid/anhydride or adducts of pentaerythritol, or mixtures of any of the foregoing. The salts of the di-valent or tri-valent metals are derived from any of the following: calcium, magnesium, iron, zinc, aluminum, manganese and barium, or mixtures of any of these.

The waxes may be of natural origin, meaning they may be animal, vegetable or mineral. Animal waxes include beeswax, lanolin, shellac wax and Chinese insect wax. Vegetable wax includes carnauba, candelilla, bayberry, and sugar cane waxes. Mineral wax includes fossil or earth waxes, including ozocerite, ceresin and montan, or petroleum waxes, including paraffin and microcrystalline waxes. Alternatively, the waxes may be synthetic, or mixtures of natural and synthetic waxes. For instance, particular coating materials may include a low-molecular weight partially oxidized polyethylene, which is preferably co-melted with paraffin, low-molecular weight poly(ethylene/acrylic acid) or low-molecular weight poly(ethylene/methacrylic acid). It should be noted that the coating material may be any one of the waxes described in this paragraph, or a mixture of any of them.

The fatty derivatives may be either fatty acids, fatty metallic salts of these fatty acids, fatty acid amides, fatty alcohols and fatty esters, or mixtures of any of the foregoing. In this context, "fatty" means long-chain aliphatic. In particular, the acid may be a carboxylic acid, such as stearic acid, and the salts may be calcium, magnesium, zinc or aluminum salts. The acid amide may be stearamide. The alcohol may be stearyl alcohol. The ester is formed from reaction of a long-chain acid with a long-chain alcohol. The ester may be a fatty acid ester of a fatty alcohol or a fatty acid ester of glycerol.

Sterols as such, or long-chain sterol esters, meaning an ester formed from a sterol, may also be used as the coating material. In either case, the sterols may be of animal origin (e.g., cholesterol) or of plant origin (e.g., ergosterol).

When wood rosin, rosin derivatives, waxes, fatty derivatives, sterols, long-chain sterol esters or sulfur are used as the coating material, the coating material has a melting point within the range of 55–220° C. When one is within 20° C. of the melting point, the molten coating material does not decompose and is film-forming, but not filament-forming. A lab test for film-forming and filament forming can be described as follows: The first part of the test consists of melting the test coating material in a small aluminum weighing dish so that upon cooling, a thin continuous film (1 mm. or less in thickness) is formed, even when there is not enough material to span the bottom of the dish. The second part of the test consists of dipping the end of a small spatula into a one-centimeter deep mass of molten coating material and lifting the spatula end to about 2 cm. above the molten surface. The coating material is not filament forming if no strands or filaments are formed between the melt and the spatula end. This third part of the test is to hold the coating material at a temperature where the material is film forming, but not filament forming, to demonstrate that at least under a nitrogen blanket, no significant degradation occurs, which is indicated by off gas, thickening, etc., at this temperature for 10 minutes or longer. Finally, the temperature where the molten coating material is held should be no higher than 20° C. of the melting point of the coating material.

The coating material of the present invention is insoluble in water. Water insoluble means those coating materials which have a solubility in water of $\leq 5\%$ at 25° C. Thus, although it is preferred to coat solid particles using a coating material as a melt, those coating materials containing pendant carboxylic acid groups (e.g., rosin, oxidized polyethylene, fatty acids) may be applied from an aqueous solution containing ammonia. As the ammonia is flashed off during the coating process, the original water-insoluble coating material is deposited on the solid particles.

Alternatively, the coating material of the crop protection composition of the first embodiment may be a water-insoluble synthetic latex polymer, or carboxylated versions thereof. A latex is a colloidal aqueous suspension of a polymer resulting from emulsion polymerization of one or more hydrophobic monomers in the presence of a surfactant and an initiator, forming small islands of plasticized polymer. These small islands coalesce and form a continuous film coating on the surface of the solid particle during processing, while the water is flashed off.

In one version of this alternative of the first embodiment, the water insoluble synthetic latex polymer may be either a homopolymer of a first group of monomers, or a copolymer made from the first group of monomers combined with at least one monomer from a second group of monomers. The second group of monomers includes monomers which are used to make copolymers by using at least one member of the first group of monomers. The first group of monomers is hydrophobic, and the second group of monomers is hydrophilic. The first group of monomers includes ethylene; propylene; styrene; alpha-methylstyrene; vinyl chloride; alkyl acrylate; alkyl methacrylate; vinyl acetate; tetrafluoroethylene, acrylonitrile; alkylene, including butylene, isobutylene, isoprene and butadiene; chloroprene, divinylbenzene and vinyl alkyl ($\geq$C10) esters. The second group of monomers includes acrylic acid, methacrylic acid, vinyl alcohol, vinyl pyrrolidone and acrylamide.

Examples of co-polymers of the first and second groups of monomers include poly(ethylene/acrylic acid), poly(ethylene/methacrylic acid), poly(stearyl methacrylate/acrylic acid), poly(stearyl methacrylate/methacrylic acid), poly(styrene/maleic anhydride), poly(ethylene/vinyl alcohol), poly(alpha-alkene) ($\geq$C10)/vinyl pyrrolidone), poly(ethylene/maleic anhydride), poly(ethylene/vinyl acetate), poly(styrene/acrylonitrile) and poly(styrene/acrylonitrile/butadiene).

In another version of the alternative of the first embodiment, the water-insoluble synthetic latex polymer may be either poly(ethylene terephthalate), polyamide resin, synthetic polyterpene, synthetic poly (beta-pinene), cellulose esters, including cellulose acetate and cellulose acetate/butyrate.

The mononucleate solid crop protection particle of the present invention may be an individual crystalline solid particle. Moreover, it may be a crop protection chemical. Examples of such crop protection chemicals include herbicides, insecticides, acaricides, miticides, fungicides, nematicides and plant growth regulators. Alternatively, the solid crop protection particle of the present invention may be a crop protection microbial. Such microbials include beneficial viruses, bacteria, nematodes, fungi and protozoa.

Moreover, instead of a solid particle, the solid particle may comprise a low-melting active and a porous, solid inert carrier particle, where the low-melting active is absorbed onto the porous, solid inert carrier particle. By "low-melting active" is meant a material which is not a solid at room temperature, or at least, a material which is easily softened.

In particular, the solid crop protection particle may be bromacil (5-bromo-3-sec-butyl-6-methyluracil) (International Union of Pure and Applied Chemistry (IUPAC). Alternatively, the solid crop protection particle may be a herbicide, such as a sulfonylurea. The sulfonylurea may be, but is not limited to, the following: tribenuron-methyl, thifensulfuron, metsulfuron-methyl, bensulfuron-methyl, chlorimuron-ethyl, rimsulfuron and azimsulfuron. In a preferred embodiment of the present invention, the sulfonylurea herbicide is tribenuron-methyl, and the coating material is a mixture of partially oxidized, low-molecular weight polyethylene, which is sold by Eastman Chemical Co. of Kingsport, Tenn. as EPOLENE E10 (hereinafter referred to as "EPOLENE E10"), and paraffin. In another preferred embodiment of the present invention, the sulfonylurea herbicide is tribenuron-methyl, and the coating material is wood rosin.

With the present invention, the coated solid particles of the composition may be bonded together via water dispersible bridges in the form of water dispersible granules. These granules disperse to small individual coated particles in a mi: tank of water, so that they may be sprayable without screen or nozzle pluggage. This enables sprayability, since it is necessary for the composition to disperse to the individual coated particles when mixed with water in a mix tank before spraying. It also enhances biological efficacy of the particles, since they are not agglomerated.

The composition of the present invention may be made into a wettable powder by adding adjuvants such as surfactants, wetting agents, dispersants and diluents. The wettable powder may also be formed into a water-dispersible granule. This may be done by any of the conventional methods in the art such as compaction, which is preferred, melt or paste extrusion, pan granulation or a fluidized bed. Particle agglomeration occurs in water-dispersible granules, but the particle-to-particle bonds are water-dispersible. The wettable powder may be packaged in conventional containers or preferably as water soluble bags. This allows one to add a soluble bag to a mix tank without encountering dust, which so often accompanies handling particles of very small size.

As noted above, the coating materials of the present invention are water-insoluble. This avoids rapid water pickup from the air. However, the coating materials are water-permeable enough as a thin coating to effectively release the crop protection solid particle upon brief mixing in a mix tank with water, and/or upon contact with dew, once deposited on the target plant or soil. Thus, when faster release of the solid particle, especially an active, is desired, then less hydrophobic and/or thinner and more permeable coatings can be used, e.g., ≦20%, and usually ≦10%. This ensures immediate availability of the crop protection solid particle upon mixing with water in a mix tank. If a controlled release formulation is desired upon spraying on the crop or ground, a thicker or more hydrophobic coating may be chosen. In this case, the crop protection solid particle would be slowly released upon exposure to rain or dew. When an insecticide is used as the controlled release solid particle, it can be released upon ingestion and extraction in the insect gut.

Further in accordance with a second embodiment of the present invention, there is provided a crop protection mixture. The mixture comprises a crop protection partner. The partner is a solid particle, and it may be either a chemical or a microbial partner. The solid particle may comprise a low-melting active and a solid, inert carrier particle, where the low-melting active is absorbed on the solid inert carrier particle. In addition, the mixture comprises a crop protection composition, as described above with respect to the first embodiment. The partner ordinarily degrades the solid crop protection particle when stored or aged together as a mixture. The present invention prevents the solid crop protection particle from degrading when it comes into contact with the partner.

With the crop protection mixture of the second embodiment, it is possible to have a water-dispersible granule of a crop protection composition mixed or stored with a partner, in the form of a powder, a water-dispersible granule of the partner mixed or stored with the crop protection composition, in the form of a powder, a water-dispersible granule of the crop protection composition mixed or stored with a water-dispersible granule of the partner, or a single water-dispersible granule containing particles of the crop protection composition and the partner. The key requirement of the present invention is that each of these water-dispersible granules disperse into the individual coated particles or the partner particles when added to water in a mi: tank.

As with the crop protection composition as described above, the coated solid particles of either the crop protection composition or the crop protection mixture, which may be in the form of a powder, may be made into a wettable powder by adding adjuvants such as surfactants, wetting agents, dispersants and diluents. The wettable powder may also be formed into a water-dispersible granule. This may be done by any of the conventional methods in the art such as compaction, which is preferred, melt or paste extrusion, pan granulation or a fluidized bed. As noted above with respect to the first embodiment, particle agglomeration occurs in water-dispersible granules, but the particle-to-particle bonds are water-dispersible. As with the crop protection composition, the wettable powder form of the crop protection mixture of the present invention may be packaged in conventional containers or preferably as water soluble bags. The crop protection composition or the partner particles, or both, are individually or mutually stored in the mixture as water dispersible granules.

The partner may be a herbicide, such as a hormonal, anticholinesterase, or of the glyphosate family. Examples of hormonals include phenoxies, such as 2,4-D (2,4-dichlorophenoxyacetic acid) derivatives, especially the sodium or acid form, and MCPA [(4-chloro-2-methylphenoxy)acetic acid]. Examples of anticholine esterases include organophosphorous herbicides, such as anilofos. The partner may be a solid particle or it may comprise a low-melting active and a porous solid inert carrier particle, where the active is absorbed onto the porous solid inert carrier particle.

As discussed above, the solid crop protection particle of the composition may be a crop protection chemical. Examples of such crop protection chemicals include herbicides, insecticides, acaricides, miticides, fungicides, nematicides and plant growth regulators. Alternatively, the solid crop protection particle of the present invention may be a crop protection microbial. Such microbials include beneficial viruses, bacteria, nematodes, fungi and protozoa.

In particular, the crop protection solid particle of the composition may be a herbicide, such as a sulfonylurea. The sulfonylurea may be, but is not limited to, the following: tribenuron-methyl, thifensulfuron, metsulfuron-methyl, bensulfuron-methyl, chlorimuron-ethyl, rimsulfuron and azimsulfuron. It is preferable that the ratio of the weight of the sulfonylurea to the weight of the partner is in the range of about 1/10 to 1/200. In one preferred embodiment, the partner is 2,4-D (2,4-dichloro-phenoxyacetic acid), and the composition comprises tribenuron-methyl coated with a mixture of partially oxidized, low-molecular weight polyethylene (EPOLENE E10) and paraffin. In another preferred embodiment, the partner is 2,4-D (2,4-dichlorophenoxyacetic acid), and the composition comprises tribenuron-methyl coated with wood rosin.

Figure 2:
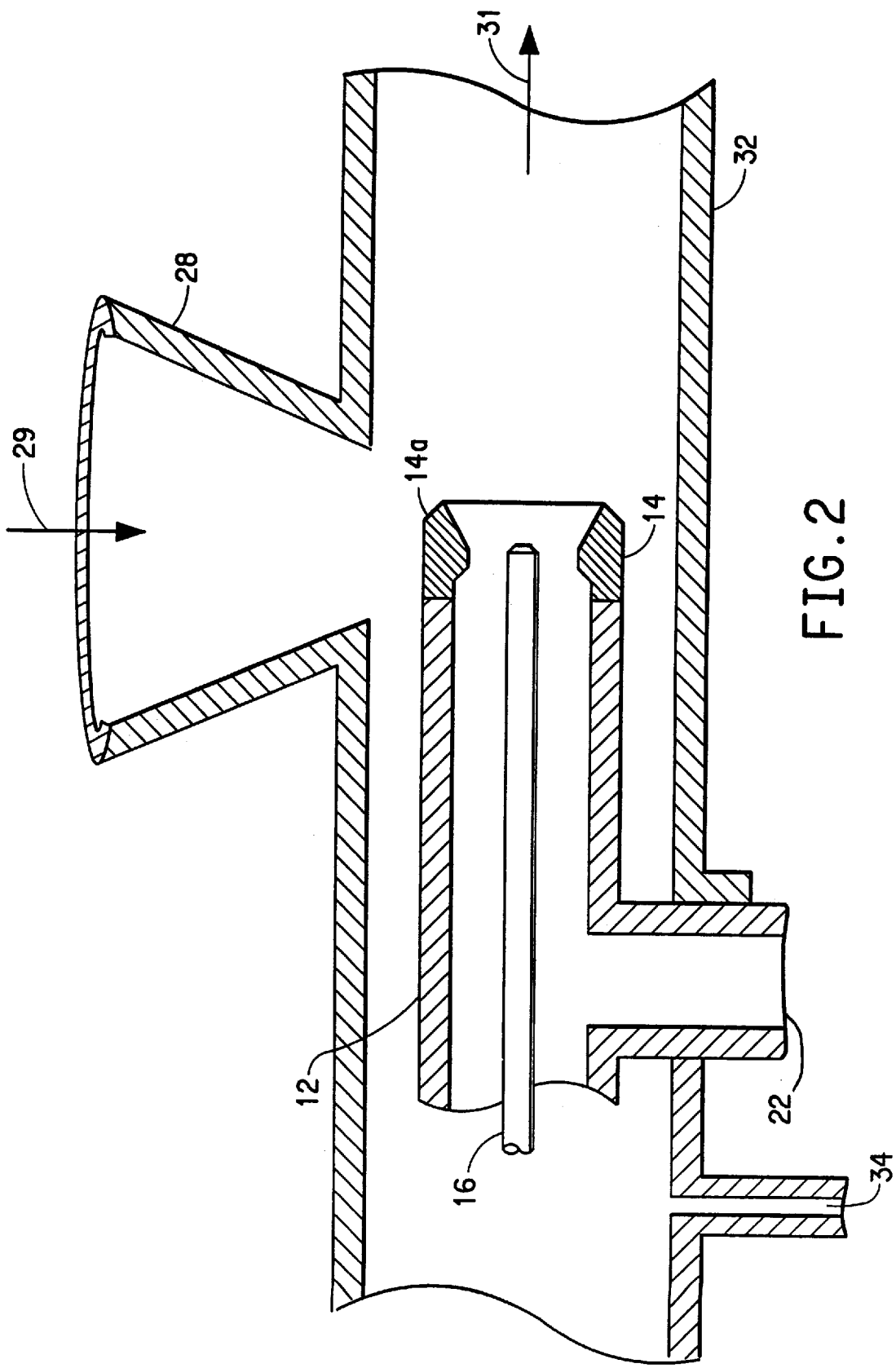
FIG. 2 is a cut-away, expanded, cross-sectional view of a portion of the apparatus shown in FIG. 1.

Reference will now be made in detail to an apparatus and a process suitable for making the above-described crop protection composition. An example of such apparatus is illustrated in FIGS. 1 and 2. By coating is meant adhering a layer of one substance to the surface of a solid particle, and includes encapsulation of substantially all, or all, the surface of the solid particle. It should be noted, that while one pass or cycle of the process of the present invention completely coats or encapsulates the solid particle, more than one pass may be used to adhere additional coating material to the solid particle, depending on the desired thickness of the coating.

The apparatus and the process of the present invention may be used to make a crop protection composition comprising a solid crop protection solid particle coated with a coating material. In particular, the apparatus and process may be used to make a coated particle having a diameter in the range of about 0.5 to 50 m, and preferably less than about 30 m. The coated solid crop protection particle made by the process of the present invention encompasses any crop protection solid particle and any coating material. The solid particle may be either a chemical crop protection solid particle, such as a herbicide, an acaricide, an insecticide, a miticide, a plant growth regulator, a fungicide or a nematicide, or a microbial crop protection solid particle, such as beneficial viruses, nematodes, fungi, bacteria or protozoa. The coating material may be either wood rosin, rosin derivatives, waxes, fatty derivatives, sterols, long-chain sterol esters and sulfur, as described above. Alternatively, the coating material may comprise either version of a water-insoluble synthetic latex as described above.

The apparatus and process as described hereinbelow are particularly useful for making coated crop protection solid particles which in particular have heretofore been too small in diameter to achieve, say those having a diameter in the range of 0.5 to 50 micrometers ($\mu$), and in particular those having a diameter of less than 30 micrometers ($\mu$). Moreover, with the apparatus and the process of the present invention, the force of the gas stream may be varied so that the particles released into the zone of turbulence do not stick to each other, resulting in a composition in which there is only one individual solid particle in the core of each coating. Also, the coated solid particles are non-agglomerated, so that two or more individual particles are not stuck together by the coating. This non-agglomeration, in particular, where the coated particles have a diameter in the range of about 0.5 to 50 micrometers ($\mu$), was heretofore not possible with processes of the prior art. Thus, the size distribution of non-agglomerated, coated solid particles made by the apparatus and process of the present invention is such that a greater percentage of coated particles have a smaller diameter than could be previously achieved by processes of the prior art.

One implementation of the apparatus and process as described below enable a very small crystalline solid particle to be directly coated with a coating material, without the need for a suspension liquid, which is used in the prior art. In this implementation, which is the preferred implementation for the present invention, the coating material is in melt form before it is coated onto the solid particle. By melt is meant any substance at a temperature at or above its melting point, but below its boiling point. When the coating material is a melt, a liquid consisting of or comprising the coating material (meaning the liquid may include components other than just the coating material) is used in the apparatus and process of the present invention. A less preferred form for the coating material of the present invention is where the coating material is undissolved in a liquid, i.e., a slurry, where the slurry may comprise components other than the coating material. Examples of a slurry include an aqueous latex, or a colloidal form of a slurry, as described above. The least preferred form for the coating material of the present invention is where the coating material is dissolved in a liquid, i.e., a solution, where the solution may comprise components other than the coating material. An example of a solution is aqueous ammonia.

An apparatus for coating a solid crop protection particle with a coating material in accordance with the present invention is shown generally at 10 in FIG. 1. The apparatus of the present invention comprises a first chamber, shown at 12 in FIGS. 1 and 2. A flow restrictor 14 is disposed at one end of the first chamber. The flow restrictor is typically disposed at the downstream end of the first chamber, as shown in FIGS. 1 and 2. Flow restrictor 14 has an outlet end 14a, as shown in the detailed view of FIG. 2. Although the flow restrictor is shown as a different element from the first chamber, it may be formed integrally therewith, if desired. The flow restrictor of the present invention may have various configurations, as long as it serves to restrict flow and thereby increase the pressure of the fluid passing through it. Typically, the flow restrictor of the present invention is a nozzle.

A first, or liquid, inlet line 16 as shown in FIGS. 1 and 2 is disposed in fluid communication with the first chamber for metering a liquid comprising a coating material into the chamber. Liquid inlet line 16 meters the coating material into first chamber 12 in the outlet of flow restrictor 14, and preferably to the center of the flow restrictor when viewed along the axial length thereof. The liquid comprising the coating material is metered through liquid inlet line 16 by a metering pump 18 from a storage container 20 containing the liquid as shown in FIG. 1. It should be noted that when the coating material is a melt, storage container 20 must be heated to a temperature above the melt temperature of the coating material in order to maintain the coating material in melt form. The apparatus for coating a solid particle further includes a second, or gas, inlet line 22 disposed in fluid communication with the first chamber as shown in FIGS. 1 and 2. Generally, the gas inlet line should be disposed in fluid communication with the first chamber upstream of the flow restrictor. Gas inlet line 22 injects a first gas stream through the flow restrictor to create a zone of turbulence at the outlet of the flow restrictor. The turbulence subjects the coating material to shear forces that atomize the liquid comprising the coating material.

The first gas stream should have a stagnation pressure sufficient to accelerate the gas to at least one-half the velocity of sound, or greater, prior to entering the flow restrictor to ensure that a zone of turbulence of sufficient intensity will be formed at the outlet of the flow restrictor. The velocity of sound for a particular gas stream, e.g., air or nitrogen, will be dependent on the temperature of the gas stream. This is expressed by the equation for the speed of sound, c:

$$c = \sqrt{kgRT} \tag{1}$$

where:
 k=ratio of specific heats for the gas
 g=acceleration of gravity
 R=universal gas constant
 T=absolute temperature of the gas Thus, the acceleration of the first gas stream is dependent on the temperature of the gas.

As noted above, it is the pressurized gas that causes the atomization of the liquid comprising the coating material. The pressure of this liquid in the liquid inlet line just needs to be enough to overcome the system pressure of the gas stream. It is preferable that the liquid inlet line has an extended axial length before the zone of turbulence. If the liquid inlet line is too short, the flow restrictor becomes plugged.

The apparatus of the present invention also comprises means disposed in the second inlet line and upstream of the flow restrictor for heating the first gas stream prior to injection through the flow restrictor. Preferably, the heating means comprises a heater 24 as shown in FIG. 1. Alternatively, the heating means may comprise a heat exchanger, a resistance heater, an electric heater, or any type of heating device. Heater 24 is disposed in second inlet line 22. A pump 26 as shown in FIG. 1 conveys the first gas stream through heater 24 and into first chamber 12. When the coating material is a melt, the gas stream should be heated to a temperature at or above the melt temperature of the melt, to keep the melt in liquid (i.e., melt) form. When using a melt, it is also helpful if auxiliary heat is provided to the first inlet line which supplies the melt prior to injection, to prevent pluggage of the line.

The apparatus of the present invention further includes a hopper 28 as shown in FIGS. 1 and 2. Hopper 28 introduces a solid particle, and in particular, a solid crystalline particle, to the zone of turbulence. It is preferable that the outlet end of the flow restrictor is positioned in the first chamber beneath the hopper at the center line of the hopper. This serves to ensure that the solid particles are introduced directly into the zone of turbulence. This is important because it increases operability by providing a configuration for feeding the solid particles most easily. Moreover, as noted above, the turbulence subjects the liquid comprising the coating material to shear forces that atomize this liquid. In addition, the shear forces disperse and mix the atomized liquid with the solid particles, which allows the particles to be coated. It should be noted that with the present invention, when the coating material is in melt form, it is possible to directly coat the solid particle with the melt, without the use of a suspension liquid. Hopper 28 may be fed directly from a storage container 30 as shown by arrow 29 in FIG. 1. The hopper of the present invention may include a metering device for accurately metering the particles at a particular ratio to the liquid feed from liquid inlet line 16 into the zone of turbulence. This metering establishes the level of coating on the solid particle. Typically, the hopper of the present invention is open to the atmosphere. When the coating material is a melt, it is preferred that the solid particles are at ambient temperature because this facilitates solidification of the melt after the melt, which is initially at a higher temperature, coats the solid particle in the zone of turbulence.

The apparatus of the present invention may further include a second chamber 32 surrounding the first chamber as shown in FIGS. 1 and 2. In addition, the second chamber encloses the zone of turbulence. Second chamber 32 has an inlet 34 for introducing a second gas stream into the second chamber. The inlet of the second chamber is preferably positioned at or near the upstream end of second chamber 32. The outlet of second chamber 32 is connected to a collection container, such as that shown at 36 in FIG. 1. The second gas stream cools and conveys the coated solid particles toward the collection container as illustrated by arrow 31 in FIG. 2. In particular, when a solution or slurry is used, the solid of the solution or slurry cools between the zone of turbulence and container to form a solid coating on the particle by the time the particle reaches the container. When a melt is used, the coating material cools between the zone of turbulence so that by the time the particle reaches the container, the solid coating is formed on the particle. The first gas stream, as well as the second gas stream, are vented through the top of collection container 36.

For the configuration as shown in FIGS. 1 and 2, inlet 34 may be connected to a blower, not shown, which supplies the second gas stream to the second chamber. However, the blower and second chamber 32 may be eliminated, and the first gas stream may be used to cool he particles and to convey them to container 36. In this case, the solid from the solution or slurry or the melt cools and solidifies on the particle in the atmosphere between the zone of turbulence and the collection container, and the coated particles fall into collection container 36.

It is preferable that the axial length of the zone of turbulence is about ten times the diameter of the second chamber. This allows the pressure at the outlet of the flow restrictor to be at a minimum. Solid particles are fed into second chamber 32 as shown in FIGS. 1 and 2 near the outlet of the flow restrictor, which is preferably positioned at the center line of the hopper. If the pressure at the outlet is too great, the solid particles will back flow into the hopper.

The pressure of the second gas stream must be sufficient to assist in conveying the coated solid particles from the zone of turbulence to the collection zone, but should be lower than the pressure of the first gas stream. This is because a high relative velocity difference between the first gas stream and the second gas stream produces a sufficient degree of turbulence to coat the solid particles.

Further in accordance with the present invention, there is provided a process for coating a solid crop protection particle with a coating material. It should be noted that the process of the present invention may be practiced using the apparatus illustrated in FIGS. 1 and 2, although it should be understood that the process of the present invention is not limited to the illustrated apparatus.

The process comprises the steps of metering a liquid comprising a coating material into a flow restrictor, such as flow restrictor 14 as shown in FIGS. 1 and 2. The process of the present invention further comprises injecting a gas stream, for instance from a gas inlet line such as that shown at 22 in FIGS. 1 and 2, through the flow restrictor concurrently with metering the liquid comprising the coating material into the flow restrictor, to create a zone of turbulence at the outlet of the flow restrictor. The shear in the zone of turbulence atomizes the liquid comprising the coating material.

The gas stream is heated prior to injecting it through the flow restrictor. The gas stream may be heated by a heater, such as heater 24 as shown in FIG. 1. As noted above for the apparatus, when the liquid comprising the coating material is either a solution or a slurry, the gas stream is heated to a temperature sufficient to vaporize the liquid of the solution or slurry and to leave the solid thereof remaining. When the coating material is in melt form, the gas stream should be heated to a temperature at or above the melt temperature of the melt, to keep the melt in liquid (i.e., melt) form. As also noted above for the apparatus, when using a melt, it is also helpful if auxiliary heat is provided to the first inlet line which supplies the melt prior to injection, to prevent pluggage of the line.

The process of the present invention also comprises the step of adding a solid particle, and in particular, a crystalline solid particle, to the zone of turbulence concurrently with the metering of the liquid comprising the coating material and the injection of the gas stream. This mixes the solid particle with the atomized liquid at the zone of turbulence. This mixing at the zone of turbulence coats the solid particle with the coating material. When the coating material used with the present invention is a melt, it is possible to directly coat the crystalline solid particle without the need for a suspension, as in the prior art. The solid particle is preferably metered in order to control the ratio of the solid and the liquid comprising the coating material, and thus the coating material, added at the zone of turbulence. This establishes the level of coating on the solid particle. When a solution or a slurry is used, such as aqueous ammoniacal solution or an aqueous latex, respectively, the heat from the heated gas stream serves to evaporate the liquid of the solution or slurry, leaving the solid thereof remaining to coat the particle. The mixing at the zone of turbulence then coats the solid particle with the remaining solid from the solution or slurry. When a melt is used, the mixing at the zone of turbulence coats the solid particle with the melt.

As noted above, the zone of turbulence is formed by the action of injecting the gas stream at high pressure through the flow restrictor. As discussed above with respect to the apparatus, it is preferable that the gas stream is accelerated to at least about one-half the velocity of sound prior to injection to ensure that a zone of turbulence of sufficient intensity will be formed at the outlet of the flow restrictor.

The residence time of the particles in the zone of turbulence is determined by the geometry of the first chamber and the amount of gas injected from the gas inlet line. The average residence time of the solid particle within the zone of turbulence is preferably less than 250 milli-seconds. More preferably, the average residence time of the solid particles within the zone of turbulence is in the range of 25 to 250 milli-seconds. Short residence times can be achieved because of the action of the zone of turbulence. The short residence times make the process of the present invention advantageous compared to conventional coating processes because the time, and hence, the cost of coating particles, are reduced. Also, the short residence time enables the use of heat sensitive solid articles, thus preventing their chemical degradation and preserving the viability of microbial solid particles.

Typically, the solid particles are fed from a hopper, such as hopper 28 as shown in FIGS. 1 and 2, which is open to the atmosphere. As noted above for the apparatus, when the coating material is a melt, it is preferred that the solid particles be at ambient temperature because this will facilitate solidification of the melt after the melt (which is initially at a higher temperature) coats the solid particle in the zone of turbulence.

The process of the present invention may further comprise the step of adding a second gas stream upstream of the zone of turbulence for cooling and conveying the coated solid particle. This second gas stream is added through a chamber, such as second chamber 32 as shown in FIGS. 1 and 2. As explained above for the apparatus, the pressure of the second gas stream must be sufficient to assist in conveying the coated solid particles from the zone of turbulence to the collection container, but should be lower than the pressure of the first gas stream in order to achieve coating. When a solution or slurry is used, the solid cools and solidifies on the particle in the second chamber between the zone of turbulence and a collection container, such as collection zone 36 as described above. When a melt is used, the melt cools and solidifies on the particle in the second chamber between the zone of turbulence and the collection container. When a second chamber is not included, the solid or the melt cools and solidifies on the particle in the atmosphere between the zone of turbulence and the collection container, and the coated particles fall into the container.

The present invention will be clarified by the following Examples, which are intended to be purely exemplary of the invention.

EXAMPLE 1

This Example is directed to encapsulating calcium carbonate with wood rosin. Calcium carbonate powder with a mean particle size of 10 micrometers (m) was coated with wood rosin using the apparatus as shown in FIGS. 1 and 2, and as described above.

Wood rosin, having a melting point of 120° C., was heated to 140° C. and held at this temperature in an insulated bath. This wood rosin was metered with a peristaltic pump at a rate of 681 g/min. The atomizing air was heated to 140° C. and used at 100 psig.

The calcium carbonate was metered in a screw feeder at a rate of 11,340 g/min to the hopper of the apparatus as shown in FIGS. 1 and 2. The wood rosin encapsulated the calcium carbonate particle at a coating level of 6%.

Uncoated calcium carbonate exposed to HCl will produce carbon dioxide gas due to chemical reaction. Encapsulation was proven by placing the encapsulated particles in a bath of hydrochloric acid (HCl). There was no immediate effervescence from the calcium carbonate indicating the complete surface protection provided by the wood rosin.

EXAMPLE 2

This Example is directed to a sulfonylurea herbicide coated with either wax or rosin coatings, which were metered in the form of a melt. In this Example, tribenuron methyl sulfonylurea herbicide, having a particle size ranging from about 2 to about 40 micrometers (m), was metered in a screw feeder at a rate of 600 g/min.

Sulfonylurea herbicide was coated with rosin at 190° C., metered with a gear pump at a rate of 75.6 g/min., corresponding to a coating level of 12.6% rosin, i.e., the weight of the rosin coating was 12.6% of the weight of the coated particle. A second batch of sulfonylurea herbicide was coated with wax at 110° C., metered with a peristaltic pump at a rate of 56.4 g/min., corresponding to a coating level of 9.4% wax. The wax was a mixture of a partially oxidized, low molecular weight polyethylene (EPOLENE E10) and paraffin. A first gas stream comprising nitrogen was injected through a flow restrictor, where the gas stream was at a pressure of 38–40 psi just before the flow restrictor.

Sulfonylurea herbicides are normally degraded in the presence of hormonal/phenoxy herbicides, such as sodium 2,4-D and 2,4-D acid. Thus, the effectiveness of the coatings to inhibit this degradation was tested by measuring the degradation of sulfonylurea herbicide when mixed in 1/20 weight mixtures with sodium 2,4-D and 2,4-D acid and aged for three weeks at 45° C. Uncoated sulfonylurea herbicide was tested in the same manner to provide a control. The results were as follows:

| PERCENTAGE RELATIVE DEGRADATION OF TRIBENURON METHYL | | | |
| --- | --- | --- | --- |
|  | Uncoated | 12.6% Rosin Coating | 9.4% Wax Coating |
| Sodium 2,4-D | 38.4% | 0.0% | 0.0% |
| 2,4-D Acid | 21.2% | 0.0% | 1.7% |

Thus, the results show coating at a level of 12.6% by weight essentially resulted in encapsulation of the particles. Generally, degradation of 5% or less is suitable for such formulations.

Additionally, the wax and rosin coated sulfonylurea was mixed with an ethoxylated silicone surfactant and water, and was then sprayed onto wild buckwheat, spring wheat and wild mustard. Both efficacy for weed injury and safety for the spring wheat was equivalent for the coated and uncoated sulfonylurea herbicides.

EXAMPLE 3

This Example is directed to a relatively water soluble herbicide, bromacil (5-bromo-3-sec-butyl-6-methyluracil), having 815 ppm water solubility, coated with stearic acid. In this Example, solid particles of bromacil, having a particle size range from less than $1\mu$ to $30\mu$ maximum diameter, was metered in a screw feeder at a rate of 1000 g/min.

The bromacil was coated with stearic acid in the form of a melt at a rate of 60 g/min. The stearic acid, which had a melting point of 70° C., was heated to 90° C. and held at this temperature in a storage container, such as storage container 20 as described above. This first pass coated material was collected and coated a second time, corresponding to a coating level of 6% and 12% coating level on the first pass and second pass, respectively, although it should be noted that it is not necessary to coat the particles with more than one pass in order to encapsulate the particles.

A gas stream comprising nitrogen was injected through a flow restrictor, such as that shown in FIGS. 1 and 2. The gas stream was at a pressure of 70 psi just before the flow restrictor.

Particle size measurements were done using a Sympatec Helos. The Helos uses forward light scattering to measure particle size distribution. A well dispersed stream of dry particles is passed through a columnated laser beam. The resulting diffraction pattern is deconvoluted into a size distribution. The table below shows the particle size analysis of uncoated bromacil, first pass coated bromacil and second pass coated bromacil.

| Particle Fraction | Microns Diameter of Coated vs. Uncoated Bromacil | | |
|---|---|---|---|
| | Uncoated Bromacil Zero Stearic Acid | First Pass 6% stearic acid | Second Pass 11.9% stearic acid |
| 5% smaller than | 0.7 | 0.8 | 0.9 |
| 10% smaller than | 1.0 | 1.2 | 1.3 |
| 16% smaller than | 1.3 | 1.8 | 1.9 |
| 50% smaller than | 4.6 | 5.5 | 5.4 |
| 90% smaller than | 12.0 | 20.0 | 19.3 |

Each of the size fractions of bromacil was coated, and the size analysis shows that the coated particles exist as individual discrete, non-agglomerated particles. The tiniest particles were still present, but with a slight increase in size as a result of being coated.

EXAMPLE 4

This Example is directed to a sulfonylurea herbicide coated with wood rosin (melting point 50–54° C.) which was then post-mixed with a low melting partner herbicide on a carrier. In this Example, chlorimuron ethyl sulfonylurea herbicide, having a particle size ranging from about 2 to about $40\mu$, was metered in a screw feeder at a rate of 1000 g/min.

Chlorimuron ethyl sulfonylurea herbicide was coated in successive passes with rosin at 185–190° C., metered with a peristatic pump at a rate of 81 g/min, corresponding to a final coating level of 27.5% rosin, i.e., the weight of the rosin coating was 27.5% of the weight of the coated particle. A first gas stream comprising nitrogen was injected through a flow restrictor, where the gas stream was at a pressure of 70 psi just before the flow restrictor.

Sulfonylurea herbicides are normally degraded in the presence of organophosphorous herbicides, such as anilofos. Thus, the effectiveness of the coating to inhibit this degradation was tested by measuring the degradation of chlorimuron ethyl sulfonylurea herbicide when mixed in 1/100 weight mixtures with anilofos (present as a 50% loaded silica) and aged for two weeks at 54° C. Uncoated chlorimuron ethyl sulfonylurea herbicide was tested in the same manner to provide a control. The results were was follows:

| PERCENTAGE RELATIVE DEGRADATION OF CHLORIMURON ETHYL | | |
|---|---|---|
| | Uncoated | 27.5% Rosin Coating |
| Anilofos on silica | 56% | 0.0% |

Thus, the results show coating at a level of 27.5% by weight essentially resulted in encapsulation of the particles

EXAMPLE 5

This Example is directed to the preparation of herbicide coated with wax which is then post-mixed with anilofos on silica, in Example 6. In this Example, metsulfuron methyl sulfonylurea herbicide, having a particle size ranging from about 2 to about $40\mu$ was metered in a screw feeder at a rate of 512 g/min.

The metsulfuron methyl was coated with was at 154° C., metered with a peristaltic pump at a rate of 64 g/min, corresponding to a coating level of 8.4% wax. The coating was a mixture of a partially oxidized, low molecular weight polyethylene (EPOLENE E10) and paraffin. A gas stream comprising nitrogen was injected through a flow restrictor, where the gas stream was at a pressure of 70 psi just before the flow restrictor.

EXAMPLE 6

In this Example, the coated sulfonylureas (5,6 from the list below) from Example 4 and 5 were post-mixed with a hammer milled mixture of anilofos, wetting agent, dispersant, and diluent (1,2,3,4 from the list below) to give a chemically stable wettable powder.

| | |
|---|---|
| 1. 60% anilofos on silica | 4.17 g |
| 2. Morwet D425* | 1.00 g |
| 3. Morwet EFW** | 0.20 g |
| 4. Celite 209*** | 4.57 g |
| 5. Wax coated metsulfuron methyl from Ex 5 | 0.028 g |
| 6. Rosin coated chlorimuron ethyl from Ex 4 | 0.035 g |

*a common anionic dispersant, condensed naphthalene sulfonate, sold under the trademark "MORWET®" D425 by the Witco Corporation of Greenwich, Connecticut
**a common anionic wetting agent, alkyl naphthalene sulfonate, sold under the trademark "MORWET®" EFW by the Witco Corporation of Greenwich, Connecticut.
***a diatomaceous earth carrier, sold under the trademark "CELITE" 209 by the Celite Corporation of Lompac, California

* a common anionic dispersant, condensed naphthalene sulfonate, sold under the trademark "MORWET®" D425 by the Witco Corporation of Greenwich, Connecticut
** a common anionic wetting agent, alkyl naphthalene sulfonate, sold under the trademark "MORWET®" EFW by the Witco Corporation of Greenwich, Connecticut.

*** a diatomaceous earth carrier, sold under the tradename "CELITE" 209 by the Celite Corporation of Lompac, Calif.

Coated metsulfuron methyl and chlorimuron ethyl (ingredients 5 and 6 in the list above) were extracted from the wettable powder (ingredients 1–6 in the list above) and each were tested by High Pressure Liquid Chromatography (HPLC) at 25° C. for their chemical identity. These coated sulfonylureas were aged at an accelerated rate for 2 weeks at 54° C. and were tested again by HPLC. As can be seen from the results below, the same amount of coated sulfonylurea was quantitated by HPLC after accelerated aging. Thus, the sulfonylureas coated in accordance with the present invention had excellent chemical stability.

Assay (HPLC)

25° C. sample-0.20% metsulfuron methyl (unaged)
54° C. sample-0.20% metsulfuron methyl (aged)
25° C. sample-0.25% chlorimuron ethyl (unaged)
54° C. sample-0.25% chlorimuron ethyl (aged)

In comparable tests on uncoated metsulfuron methyl and chlorimuron ethyl, the respective uncoated sulfonylurea decomposed during accelerated aging, so that there was much less sulfonylurea in the aged formulation.

In addition, the aged coated metsulfuron methyl and chlorimuron ethyl were tested by a Long Tube Sedimentation (LTS) test, which indicates the completeness of dispersion of a solid formulation back to individual particles. only 0.001 ml of large particles fell out of the bottom of the sedimentation tube after 1 minute, 0.002 ml fell out after 3 minutes, and 0.004 fell out after 5 minutes. Thus, the coated sulfonylureas made according to the present invention had good dispersion properties.

Additional advantages and modifications will readily occur to those skilled in the art. The invention, in its broader aspects, is therefore not limited to the specific details, representative apparatus and illustrative Examples shown and described. Accordingly, departures may be made from such details without departing from the spirit or scope of the general inventive concept as defined by the appended claims and their equivalents.

What is claimed is:

1. A crop protection composition, comprising a mononucleate crop protection solid particle coated with a water-insoluble coating material, wherein the coating material is selected from the group consisting of: wood rosin, rosin derivatives, waxes, fatty derivatives, sterols, long-chain sterol esters and sulfur, and the diameter of the crop protection composition is in the range of 0.5 to 50 micrometers.

2. The crop protection composition of claim 1, wherein the rosin derivatives are selected from the group consisting of: partially dimerized rosin, partially hydrogenated rosin, salts of di-valent metals, salts of tri-valent metals, adducts of maleic acid/anhydride, adducts of fumaric acid/anhydride and adducts of pentaerythritol.

3. The crop protection composition of claim 1, wherein the wax is selected from the group consisting of natural waxes and synthetic waxes.

4. The crop protection composition of claim 1, wherein the fatty derivatives are selected from the group consisting of acids, metallic salts of the acids, acid amides, alcohols and esters.

5. A crop protection composition, comprising a mononucleate crop protection solid particle coated with a water-insoluble coating material, wherein the coating material is a synthetic latex polymer selected from the group consisting of: a homopolymer of a first group of monomers and a co-polymer made from the first group of monomers combined with at least one monomer from a second group of monomers, and the diameter of the crop protection composition is in the range of 0.5 to 50 micrometers.

6. The crop protection composition of claim 5, wherein the first group of monomers includes ethylene, propylene, styrene, alpha-methylstyrene, vinyl chloride, alkyl acrylate, alkyl methacrylate, vinyl acetate, tetrafluoroethylene, acrylonitrile, alkylene, chloroprene, divinylbenzene and vinyl alkyl esters, and the second group includes acrylic acid, methacrylic acid, vinyl alcohol, vinyl pyrrolidone and acrylamide.

7. The crop protection composition of claim 5, wherein the second group of monomers includes acrylic acid, methacrylic acid, vinyl alcohol, vinyl pyrrolidone and acrylamide.

8. A crop protection composition, comprising a mononucleate crop protection solid particle coated with a water-insoluble coating material, wherein the coating material is a synthetic latex polymer selected from the group consisting of: poly(tethylene terephthalate), polyamide resin, synthetic polyterpene, synthetic poly(beta-pinene) and cellulose esters, and the diameter of the crop protection composition is in the range of 0.5 to 50 micrometers.

9. The crop protection composition of any of claims 1, 5 or 8, wherein the solid crop protection particle comprises a low-melting active and a porous solid inert carrier particle, and the low-melting active is absorbed onto the porous solid inert carrier particle.

10. The crop protection composition of any of claims 1, 5 or 8, wherein the solid crop protection particle is a herbicide.

11. The crop protection composition of claim 10, wherein the herbicide is a sulfonylurea.

12. The crop protection composition of claim 11, wherein the coating is a mixture of partially oxidized, low molecular weight polyethylene and paraffin, and the sulfonylurea is tribenuron methyl.

13. A process for coating a solid crop protection particle with a coating material to form a crop protection composition, the process comprising the steps of:

(a) metering a coating material into a flow restrictor;

(b) injecting a gas stream through the flow restrictor concurrently with step (a) to create a zone of turbulence at the outlet of the flow restrictor, thereby atomizing the coating material;

(c) heating the gas stream prior to injecting the gas stream through the flow restrictor; and (d) adding a solid crop protection particle to the zone of turbulence concurrently with steps (a) and (b) to mix the solid particle with the atomized coating material, wherein the mixing at the zone of turbulence coats the solid crop protection particle with the coating material to form a crop protection composition having a diameter in the range of 0.5 to 50 micrometers.

14. A product made by the process of claim 13.

15. A crop protection mixture, including:

(a) a crop protection partner comprising a solid particle; and (b) a crop protection composition comprising: a mononucleate crop protection solid particle coated with a water-insoluble coating material, wherein the coating material is a synthetic latex polymer selected from the group consisting of: a homopolymer of a first group of monomers and a co-polymer made from the first group of monomers combined with at least one monomer from a second group of monomers, and the diameter of the crop protection composition is in the range of 0.5 to 50 micrometers.

16. A crop protection mixture, including:
(a) a crop protection partner comprising a solid particle; and
(b) a crop protection composition comprising: a mononucleate crop protection solid particle coated with a water-insoluble coating material, wherein the coating material is a synthetic latex polymer selected from the group consisting of: poly(ethylene terephthalate), polyamide resin, synthetic polyterpene, synthetic poly(beta-pinene) and cellulose esters, and the diameter of the crop protection composition is in the range of 0.5 to 50 micrometers.

17. A crop protection mixture, including:
(a) a crop protection partner comprising a solid particle; and
(b) a crop protection composition comprising: a mononucleate, solid crop protection particle coated with a coating material, wherein the coating material is selected from the group consisting of: wood rosin, rosin derivatives, waxes, fatty derivatives, sterols, long-chain sterol esters and sulfur, and the diameter of the crop protection composition is in the range of 0.5 to 50 micrometers.

18. The mixture of claim 17, wherein the composition solid particle is a sulfonylurea and the ratio of the weight of the sulfonylurea to the weight of the partner is in the range of about 1/10 to 1/200.

19. The mixture of claim 18, wherein the partner is 2,4-D (2,4-dichlorophenoxyacetic acid), the sulfonylurea is tribenuron-methyl, and the coating material is a mixture of partially oxidized, low-molecular weight polyethylene and paraffin.

20. The mixture of claim 18, wherein the partner is 2,4-D (2,4-dichlorophenoxyacetic acid), the sulfonylurea is tribenuron-methyl, and the coating material is wood rosin.

* * * * *